US006451333B1

(12) United States Patent
Beerse et al.

(10) Patent No.: US 6,451,333 B1
(45) Date of Patent: *Sep. 17, 2002

(54) MILD, RINSE-OFF ANTIMICROBIAL LIQUID CLEANSING COMPOSITIONS

(75) Inventors: Peter William Beerse, Morrow; Jeffrey Michael Morgan, Springboro; Kathleen Grieshop Baier, Cincinnati; Robert Gregory Bartolo, Montgomery; Theresa Anne Bakken Schuette, Breckenridge, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/323,419

(22) Filed: Jun. 1, 1999

Related U.S. Application Data

(63) Continuation-in-part of application No. 08/869,302, filed on Jun. 4, 1997, now abandoned.

(51) Int. Cl.[7] .......................... A01N 25/00; A61K 7/00; A61K 7/50; A61K 7/40; C11D 7/50
(52) U.S. Cl. ...................... 424/405; 424/401; 510/130; 510/131; 510/138; 514/975
(58) Field of Search ................................ 424/401, 404; 510/130, 131, 138; 514/975

(56) References Cited

U.S. PATENT DOCUMENTS

| | | | |
|---|---|---|---|
| 2,999,265 A | 9/1961 | Duane et al. ................... 424/16 |
| 3,057,467 A | 10/1962 | Williams ...................... 206/46 |
| 3,398,826 A | 8/1968 | Clancy ......................... 206/46 |
| 3,563,371 A | 2/1971 | Heinz ........................... 206/46 |
| 3,881,210 A | 5/1975 | Drach et al. .............. 15/104.93 |
| 4,942,029 A | 7/1990 | Scheps ......................... 424/78 |
| 5,441,742 A | 8/1995 | Autant et al. ................ 424/405 |
| 5,620,694 A | 4/1997 | Girardot ...................... 424/402 |
| 5,629,081 A | 5/1997 | Richards et al. ............... 442/96 |
| 5,700,842 A | 12/1997 | Cole ............................ 514/721 |
| 5,744,149 A | 4/1998 | Girardot ...................... 424/402 |
| 5,780,020 A | 7/1998 | Peterson et al. ............... 424/65 |
| 5,972,361 A | 10/1999 | Fowler et al. ................ 424/402 |
| 6,063,397 A | 5/2000 | Fowler et al. ................ 424/443 |
| 6,106,851 A * | 8/2000 | Beerse et al. ................ 424/401 |
| 6,113,933 A * | 9/2000 | Beerse et al. ................ 424/404 |

FOREIGN PATENT DOCUMENTS

| | | | |
|---|---|---|---|
| EP | 0 613 675 | 9/1994 | ............ A61K/7/00 |
| GB | 2288811 | 11/1995 | ............ C11D/1/831 |
| WO | WO 93/17558 | 9/1993 | ............ A23L/2/38 |
| WO | WO 95/03781 | 2/1995 | ............ A61K/7/48 |
| WO | WO 95/24179 | 9/1995 | ............ A61K/7/00 |
| WO | WO 96/17918 | 6/1996 | ............ C11D/1/83 |
| WO | WO 96/21426 | 7/1996 | ............ A61K/7/50 |
| WO | WO 96/29983 | 10/1996 | ............ A61K/7/50 |
| WO | WO 97/03647 | 2/1997 | ............ A61K/7/50 |
| WO | WO 97/07781 | 3/1997 | ............ A61K/7/50 |
| WO | WO 97/14406 | 4/1997 | ............ A61K/7/50 |
| WO | WO 98/18445 | 5/1998 | ............ A61K/7/50 |

* cited by examiner

*Primary Examiner*—Frederick Krass
*Assistant Examiner*—Donna Jagoe
(74) *Attorney, Agent, or Firm*—Marianne Dressman; Tara Rosnell

(57) ABSTRACT

The present invention relates to a rinse-off antimicrobial cleansing composition comprising from about 0.1% to about 5.0%, by weight of the cleansing composition, of an antimicrobial active; from about 9% to about 14%, by weight of the cleansing composition, of an anionic surfactant, wherein at least about 67% of the anionic surfactant is selected from the group consisting of Class A surfactants, Class C surfactants, and mixtures thereof, wherein the ratio of Class A surfactant to Class C is from about 4:1 to about 1.5:1, and wherein the total anionic surfactant comprises less than about 50% of the ammonium counter cation salt; from about 4% to about 8%, by weight of the cleansing composition, of a proton donating agent having a Biological Activity Index, Z, of greater than about 0.75 and wherein the proton donating agent is such that the composition is essentially free of $C_4$–$C_{20}$ alkyl fatty acid; a mildness enhancing agent selected from the group consisting of from about 20% to about 70%, by weight of the anionic surfactant, of a mildness enhancing cosurfactant; form about 0.1% to about 1.0%, by weight of the cleansing composition, of a mildness enhancing polymer; and mixtures thereof; and from about 35% to about 93.9%, by weight of the cleansing composition, of water; wherein the composition is adjusted to a pH of greater than about 3.5 and less than about 4.5. The invention also encompasses methods for cleansing, removing germs and decreasing the spread of transient Gram negative and Gram positive bacteria using the rinse-off antimicrobial cleansing compositions described herein.

43 Claims, No Drawings

MILD, RINSE-OFF ANTIMICROBIAL LIQUID CLEANSING COMPOSITIONS

This is a continuation-in-part application of U.S. patent application Ser. No. 08/869,302, filed Jun. 4, 1997 now abandoned.

TECHNICAL FIELD

The present invention relates to mild, rinse-off, personal cleansing compositions which provide enhanced antimicrobial effectiveness. Specifically, the personal cleansing compositions of the invention provide previously unseen residual effectiveness against transient Gram negative bacteria, improved residual effectiveness against Gram positive bacteria and improved immediate germ reduction upon use.

BACKGROUND OF THE INVENTION

Human health is impacted by many microbial entities. Inoculation by viruses and bacteria cause a wide variety of sicknesses and ailments. Media attention to cases of food poisoning, strep infections, and the like is increasing public awareness of microbial issues.

It is well known that the washing of hard surfaces, food (e.g. fruit or vegetables) and skin, especially the hands, with antimicrobial or non-medicated soap, can remove many viruses and bacteria from the washed surfaces. Removal of the viruses and bacteria is due to the surfactancy of the soap and the mechanical action of the wash procedure. Therefore, it is known and recommended that the people wash frequently to reduce the spread of viruses and bacteria.

Bacteria found on the skin can be divided into two groups: resident and transient bacteria. Resident bacteria are Gram positive bacteria which are established as permanent microcolonies on the surface and outermost layers of the skin and play an important, helpful role in preventing the colonization of other, more harmful bacteria and fungi.

Transient bacteria are bacteria which are not part of the normal resident flora of the skin, but can be deposited when airborne contaminated material lands on the skin or when contaminated material is brought into physical contact with it. Transient bacteria are typically divided into two subclasses: Gram positive and Gram negative. Gram positive bacteria include pathogens such as *Staphylococcus aureus*, *Streptococcus pyogenes* and *Clostridium botulinum*. Gram negative bacteria include pathogens such as Salmonella, *Escherichia coli*, Klebsiella, Haemophilus, *Pseudomonas aeruginosa*, Proteus and *Shigella dysenieriae*. Gram negative bacteria are generally distinguished from Gram positive by an additional protective cell membrane which generally results in the Gram negative bacteria being less susceptible to topical antibacterial actives.

Antimicrobial cleansing products have been marketed in a variety of forms for some time. Forms include deodorant soaps, hard surface cleaners, and surgical disinfectants. These traditional rinse-off antimicrobial products have been formulated to provide bacteria removal during washing. The antimicrobial soaps have also been shown to provide a residual effectiveness against Gram positive bacteria, but limited residual effectiveness versus Gram negative bacteria.

By residual effectiveness it is meant that bacteria growth on a surface is controlled for some period of time following the washing/rinsing process. For example, antibacterial soap, when used regularly in hand washing, has been found to provide a 1.0 log to 1.5 log reduction (i.e 90 to 97% reduction) residual effectiveness against Gram positive bacteria after two to five hours. That is skin washed with antibacterial soap, was tested two to five hours later, to be contaminated with only from 3 to 10% of the number of Gram positive bacteria compared to skin washed with a placebo soap, depending on the test protocol and bacteria tested. Also, Dial or Safeguard liquid soaps, when used in hand washing, have been found to reduce the amount of the bacteria on the skin by from about 1.5 log (97%) to about 2.5 log (99.7%) as measured by standard Health Care Personal Handwash Tests (HCPHWT). That is skin washed with these soaps were contaminated with only 0.3%–3% of the number of bacteria compared to before washing. Antimicrobial liquid cleansers are disclosed in U.S. Pat. No. 4,847,072, Bissett et al., issued Jul. 11, 1989, U.S. Pat. No. 4,939,284, Degenhardt, issued Jul. 3, 1990 and U.S. Pat. No. 4,820,698, Degenhardt, issued Apr. 11, 1989. all of which are incorporated herein by reference.

Previously marketed formulations of Head & Shoulders® Dandruff Shampoo, marketed until 1994, comprised anionic surfactants, an antibacterial active and citric acid as a pH adjuster. Head & Shoulders® controlled *Pityrosorum ovale* fungus, which causes dandruff. PCT application WO 92/18100, Keegan et al., published Oct. 29, 1992 ("Keegan") and PCT application WO 95/32705, Fujiwara et al., published Dec. 7, 1995 ("Fujiwara") teach liquid skin cleansers comprising mild surfactants, antibacterial agent and acidic compounds to buffer the pH, which provide improved germ hostility. However, the use of the low levels of acid compounds therein, result in compositions which do not deliver the undissociated acid required to provide the improved antimicrobial benefits. This situation is compounded in Keegan and Fujiwara by the preference of mild surfactants, including nonionic surfactants.

Some of these antimicrobial products, especially the hard surface cleaners and surgical disinfectants, utilize high levels of alcohol and/or surfactants which have been shown to dry out and irritate skin tissues. Ideal personal cleansers should gently cleanse the skin, cause little or no irritation, and not leave the skin or hair overly dry after frequent use and preferably should provide a moisturizing benefit to the skin.

U.S. Pat. No. 3,141,821, issued to Compeau Jul. 21, 1964 and Irgasan DP 300 (Triclosan®) technical literature from Ciba-Giegy, Inc., "Basic Formulation for Hand Disinfection 89/42/01" set forth antibacterial skin cleansers compositions which could provide improved antimicrobial efficacy using certain anionic surfactants, antimicrobial actives and acids. However, the selection, therein, of highly active surfactants results in personal cleansing compositions which are drying and harsh to the skin.

Given the severe health impacts of Gram negative bacteria like Salmonella, *Escherichia coli* and Shigella, it would be highly desirable to formulate antimicrobial cleansing compositions which provide residual effectiveness versus these Gram negative bacteria, residual effectiveness versus Gram positive bacteria and improved immediate reduction of germs, and which are mild to the skin. Existing consumer products have been unable to achieve both Gram negative residual effectiveness and mildness.

Applicants have found that rinse-off antimicrobial cleansing compositions which provide such mildness and such antimicrobial effectiveness can be formulated by using known antimicrobial actives in combination with specific organic and/or inorganic acids as proton donating agents, and specific anionic surfactants, all of which are deposited on the skin. The deposited proton donating agent and anionic surfactant enhance the selected active, to provide a new level of hostility to bacteria contacting the skin.

SUMMARY OF THE INVENTION

The present invention relates to a rinse-off antimicrobial cleansing composition comprising from about 0.1% to about 5.0%, by weight of the cleansing composition, of an antimicrobial active; from about 9% to about 14%, by weight of the cleansing composition, of an anionic surfactant, wherein at least about 67% of the anionic surfactant is selected from the group consisting of Class A surfactants, Class C surfactants, and mixtures thereof, wherein the ratio of Class A surfactant to Class C is from about 4;1 to about 1.5:1, and wherein the total anionic surfactant comprises less than about 50% of the ammonium counter cation salt; from about 4% to about 8%, by weight of the cleansing composition, of a proton donating agent having a Biological Activity Index, Z, of greater than about 0.75, wherein the proton donating agent is such that the composition is essentially free of $C_4$–$C_{20}$ alkyl fatty acid; from about 20% to about 70%, by weight of the anionic surfactant, of a mildness enhancing cosurfactant; from about 35% to about 93.9%, by weight of the cleansing composition, of water, wherein the composition is adjusted to a pH of greater than about 3.5 and less than about 4.5.

The present invention also relates to methods for cleansing, reducing the number of germs on skin and decreasing the spread of transient Gram negative and Gram positive bacteria using the rinse-off antimicrobial cleansing compositions described herein.

DETAILED DESCRIPTION OF THE INVENTION

The rinse-off antimicrobial cleansing compositions of the present invention are highly efficacious for cleansing surfaces, especially the skin, provide a residual antimicrobial effectiveness versus transient Gram negative bacteria, provide a residual antimicrobial effectiveness versus Gram positive, reduction of germs on the skin, and are mild to the skin.

The term "rinse-off" is used herein to mean that the compositions of the present invention are used in a context whereby the composition is ultimately rinsed or washed from the treated surface, (e.g. skin or hard surfaces) either after or during the application of the product.

The term "antimicrobial cleansing composition" as used herein means a composition suitable for application to a surface for the purpose of removing dirt, oil and the like which additionally controls the growth and viability of transient Gram negative and Gram positive bacteria. Preferred embodiments of the present invention are cleansing compositions suitable for use on the human skin.

The compositions of the present invention can also be useful for treatment of acne. As used herein "treating acne" means preventing, retarding and/or arresting the process of acne formation in mammalian skin.

The compositions of the invention can also be useful for providing an essentially immediate (i.e., acute) visual improvement in skin appearance following application of the composition to the skin. More particularly, the compositions of the present invention are useful for regulating skin condition, including regulating visible and/or tactile discontinuities in skin, including but not limited to visible and/or tactile discontinuities in skin texture and/or color, more especially discontinuities associated with skin aging. Such discontinuities may be induced or caused by internal and/or external factors. Extrinsic factors include ultraviolet radiation (e.g., from sun exposure), environmental pollution, wind, heat, low humidity, harsh surfactants, abrasives, and the like. Intrinsic factors include chronological aging and other biochemical changes from within the skin.

Regulating skin condition includes prophylactically and/or therapeutically regulating skin condition. As used herein, prophylactically regulating skin condition includes delaying, minimizing and/or preventing visible and/or tactile discontinuities in skin. As used herein, therapeutically regulating skin condition includes ameliorating, e.g., diminishing, minimizing and/or effacing, such discontinuities. Regulating skin condition involves improving skin appearance and/or feel, e.g., providing a smoother, more even appearance and/or feel. As used herein, regulating skin condition includes regulating signs of aging. "Regulating signs of skin aging" includes prophylactically regulating and/or therapeutically regulating one or more of such signs (similarly, regulating a given sign of skin aging, e.g., lines, wrinkles or pores, includes prophylactically regulating and/or therapeutically regulating that sign).

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage. These signs may result from processes which include, but are not limited to, the development of textural discontinuities such as wrinkles, including both fine superficial wrinkles and coarse deep wrinkles, skin lines, crevices, bumps, large pores (e.g., associated with adnexal structures such as sweat gland ducts, sebaceous glands, or hair follicles), scaliness, flakiness and/or other forms of skin unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues, especially those proximate to the skin.

All percentages and ratios used herein, unless otherwise indicated, are by weight and all measurements made are at 25° C., unless otherwise designated. The invention hereof can comprise, consist of, or consist essentially of, the essential as well as optional ingredients and components described therein.

I. INGREDIENTS

The rinse-off antimicrobial cleansing compositions of the present invention comprise an antimicrobial active, an anionic surfactant, a proton donating agent, and water. These components are selected so that the efficacy and mildness requirements hereinafter defined for the compositions herein are met. The selection of each component is necessarily dependent on the selection of each of the other components. For example, if a weak acid is selected as the proton donating agent, then in order to realize an efficacious composition, either a more biologically active (but possibly less mild) surfactant must be employed, and/or a high level of acid within the prescribed range must be used and/or a particularly efficacious active must be employed and/or a higher level of deposition within the prescribed range must be employed Similarly, if a mild, but nonefficacious surfactant is employed, then a stronger acid and/or a high level of acid and/or a high level of deposition aid may be necessary to realize an efficacious composition. If a harsh surfactant is utilized, then a mildness agent may have to be utilized or a lipophilic skin moisturizer ingredient may have to be employed as the deposition aid. Each of these ingredients is described in detail as follows. Tables 1 and 2 summarize the formulation preferences which are required to achieve this balance.

A. Antimicrobial Active

The rinse-off antimicrobial cleansing compositions of the present invention comprise from about 0.1% to about 5.0%, preferably from about 0.1% to about 2.0%, more preferably from about 0.1% to about 1.0% of an antimicrobial active. Non-cationic actives are required in order to avoid interaction with the anionic surfactants of the invention.

Given below are examples of non-cationic antimicrobial agents which are useful in the present invention.

Pyrithiones, especially the zinc complex (ZPT)
Octopirox®
Dimethyldimethylol Hydantoin (Glydant®)
Methylchloroisothiazolinone/methylisothiazolinone (Kathon CG®)
Sodium Sulfite
Sodium Bisulfite
Imidazolidinyl Urea (Germall 115®)
Diazolidinyl Urea (Germaill II®)
Benzyl Alcohol
2-Bromo-2-nitropropane-1,3-diol (Bronopol®)
Formalin (formaldehyde)
Iodopropenyl Butylcarbamate (Polyphase P100®)
Chloroacetamide
Methanamine
Methyidibromonitrile Glutaronitrile (1,2-Dibromo-2,4-dicyanobutane or Tektamer®)
Glutaraldehyde
5-bromo-5-nitro-1,3-dioxane (Bronidox®)
Phenethyl Alcohol
o-Phenylphenol/sodium o-phenylphenol
Sodium Hydroxymethylglycinate (Suttocide A®)
Polymethoxy Bicyclic Oxazolidine (Nuosept C®)
Dimethoxane
Thimersal
Dichlorobenzyl Alcohol
Captan
Chlorphenenesin
Dichlorophene
Chlorbutanol
Glyceryl Laurate
Halogenated Diphenyl Ethers
   2,4,4'-trichloro-2'-hydroxy-diphenyl ether (Triclosan® or TCS)
   2,2'-dihydroxy-5,5'-dibromo-diphenyl ether
Phenolic Compounds
   Phenol
   2-Methyl Phenol
   3-Methyl Phenol
   4Methyl Phenol
   4-Ethyl Phenol
   2,4-Dimethyl Phenol
   2,5-Dimethyl Phenol
   3,4-Dimethyl Phenol
   2,6-Dimethyl Phenol
   4-n-Propyl Phenol
   4-n-Butyl Phenol
   4-n-Amyl Phenol
   4-tert-Amyl Phenol
   4-n-Hexyl Phenol
   4-n-Heptyl Phenol
Mono- and Poly-Alkyl and Aromatic Halophenols
   p-Chlorophenol
   Methyl p-Chlorophenol
   Ethyl p-Chlorophenol
   n-Propyl p-Chlorophenol
   n-Butyl p-Chlorophenol
   n-Amyl p-Chlorophenol
   sec-Amyl p-Chlorophenol
   n-Hexyl p-Chlorophenol
   Cyclohexyl p-Chlorophenol
   n-Heptyl p-Chlorophenol
   n-Octyl p-Chlorophenol
   o-Chlorophenol
   Methyl o-Chlorophenol
   Ethyl o-Chlorophenol
   n-Propyl o-Chlorophenol
   n-Butyl o-Chlorophenol
   n-Amyl o-Chlorophenol
   tert-Amyl o-Chlorophenol
   n-Hexyl o-Chlorophenol
   n-Heptyl o-Chlorophenol
   o-Benzyl p-Chlorophenol
   o-Benxyl-m-methyl p-Chlorophenol
   o-Benzyl-m, m-dimethyl p-Chlorophenol
   o-Phenylethyl p-Chlorophenol
   o-Phenylethyl-m-methyl p-Chlorophenol
   3-Methyl p-Chlorophenol
   3,5-Dimethyl p-Chlorophenol
   6-Ethyl-3-methyl p-Chlorophenol
   6-n-Propyl-3-methyl p-Chlorophenol 6-iso-Propyl-3-methyl p-Chlorophenol
2-Ethyl-3,5-dimethyl p-Chlorophenol
6-sec-Butyl-3-methyl p-Chlorophenol
2-iso-Propyl-3,5-dimethyl p-Chlorophenol
6-Diethylmethyl-3-methyl p-Chlorophenol
6iso-Propyl-2-ethyl-3-methyl p-Chlorophenol
2-sec-Amyl-3,5-dimethyl p-Chlorophenol
2-Diethylmethyl-3,5-dimethyl p-Chlorophenol
6-sec-Octyl-3-methyl p-Chlorophenol
p-Chloro-m-cresol
p-Bromophenol
Methyl p-Bromophenol
Ethyl p-Bromophenol
n-Propyl p-Bromophenol
n-Butyl p-Bromophenol
n-Amyl p-Bromopbenol
sec-Amyl p-Bromophenol
n-Hexyl p-Bromophenol
Cyclohexyl p-Bromophenol
o-Bromophenol
tert-Amyl o-Bromophenol
n-Hexyl o-Bromophenol
n-Propyl-m,m-Dimethyl o-Bromophenol
2-Phenyl Phenol
4-Chloro-2-methyl phenol
4-Chloro-3-methyl phenol
4Chloro-3,5-dimethyl phenol
2,4-Dichloro-3,5-dimethylphenol
3,4,5,6-Terabromo-2-methylphenol
5-Methyl-2-pentylphenol
4-Isopropyl-3-methylphenol
Para-chloro-meta-xylenol (PCMX)
Chlorothymol
Phenoxyethanol
Phenoxyisopropanol
5-Chloro-2-hydroxydiphenylmethane
Resorcinol and its Derivatives
　Resorcinol
　Methyl Resorcinol
　Ethyl Resorcinol
　n-Propyl Resorcinol
　n-Butyl Resorcinol
　n-Amyl Resorcinol
　n-Hexyl Resorcinol
　n-Heptyl Resorcinol
　n-Octyl Resorcinol
　n-Nonyl Resorcinol
　Phenyl Resorcinol
　Benzyl Resorcinol
　Phenylethyl Resorcinol
　Phenylpropyl Resorcinol
　p-Chlorobenzyl Resorcinol
　5-Chloro 2,4-Dihydroxydiphenyl Methane
　4'-Chloro 2,4-Dihydroxydiphenyl Methane
　5-Bromo 2,4-Dihydroxydiphenyl Methane
　4'-Bromo 2,4-Dihydroxydiphenyl Methane
Bisphenolic Compounds
　2,2'-Methylene bis(4-chlorophenol)
　2,2'-Methylene bis(3,4,6-trichlorophenol)
　2,2'-Methylene bis(4chloro-6-bromophenol)
　bis(2-hydroxy-3,5-dichlorophenyl)sulphide
　bis(2-hydroxy-5-chlorobenzyl)sulphide
Benzoic Esters (Parabens)
　Methylparaben
　Propylparaben
　Butylparaben
　Ethylparaben
　Isopropylparaben
　Isobutylparaben
　Benzylparaben
　Sodium Methylparaben
　Sodium Propylparaben
Halogenated Carbanilides
　3,4,4'-Trichlorocarbanilides (Triclocarban®or TCC)
　3-Trifluoromethyl-4,4'-dichlorocarbanilide 3,3',4-Trichlorocarbanilide Another class of antibacterial agents, which are useful in the present invention, are the so-called "natural" antibacterial actives, referred to as natural essential oils. These actives derive their names from their natural occurrence in plants, Typical natural essential oil antibacterial actives include oils of anise, lemon, orange, rosemary, wintergreen, thyme, lavender, cloves, hops, tea tree, citronella, wheat, barley, lemongrass, cedar leaf, cedarwood, cinnamon, fleagrass, geranium, sandalwood, violet, cranberry, eucalyptus, vervain, peppermint, gum benzoin, basil, fenncl, fir, balsam, menthol, ocmea origanum, *Hydastis carradensis, Berberidaceae daceae*, Ratanhiae and *Curcuma longa*. Also included in this class of natural essential oils are the key chemical components of the plant oils which have been found to provide the antimicrobial benefit These chemicals include, but are not limited to anethol, catechole, camphene, thymol, eugenol, eucalyptol, ferulic acid, farnesol, hinokitiol, tropolone, limonene, menthol, methyl salicylate, carvacol, terpineol, verbenone, berberine, ratanhiae extract, caryophellene oxide, citronella acid, curcumin, nerolidol and geraniol.

Additional active agents are antibacterial metal salts. This class generally includes salts of metals in groups 3b–7b, 8 and 3a–5a. Specifically are the salts of aluminum, zirconium, zinc, silver, gold, copper, lanthanum, tin, mercury, bismuth, selenium, strontium, scandium, yttrium, cerium, praseodymium, neodymium, promethum, samarium, europium, gadolinium, terbium, dysprosium, holmium, erbium, thulium, ytterbium, lutctium and mixtures thereof.

Preferred antimicrobial agents for use herein are the broad spectrum actives selected from the group consisting of Triclosan®, Triclocarban®, Octopirox®, PCMX, ZPT, natural essential oils and their key ingredients, and mixtures thereof. The most preferred antimicrobial active for use in the present invention is Triclosan®.

B. Anionic Surfactant

The rinse-off antimicrobial cleansing compositions of the present invention comprise from about 4% to about 18%. Without being limited by theory, it is believed that the anionic surfactant disrupts the lipid in the cell membrane of the bacteria. The particular acid used herein reduces the negative charges on the cell wall of the bacteria, crosses through the cell membrane, weakened by the surfactant, and acidifies the cytoplasm of the bacteria. The antimicrobial active can then pass more easily through the weakened cell wall, and more efficiently poison the bacteria.

Nonlimiting examples of anionic lathering surfactants useful in the compositions of the present invention are disclosed in McCutcheon's, Detergents and Emulsifiers, North American edition (1990), published by The Manufacturing Confectioner Publishing Co.; McCutcheon's, Functional Materials, North American Edition (1992); and U.S. Pat. No. 3,929,678, to Laughlin et al., issued Dec. 30, 1975, all of which are incorporated by reference.

A wide variety of anionic surfactants are potentially useful herein. Nonlimiting examples of anionic lathering surfactants include those selected from the group consisting of alkyl and alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and mixtures thereof. Mixtures of anionic surfactants can be used effectively in the present invention.

Anionic surfactants for use in the cleansing compositions include alkyl and alkyl ether sulfates. These materials have the respective formulae $R^1O$—$SO_3M$ and $R^1(CH_2H_4O)_x$—$O$—$SO_3M$, wherein $R^1$ is a saturated or unsaturated, branched or unbranched alkyl group from about 8 to about 24 carbon atoms, x is 1 to 10, and M is a water-soluble cation such as ammonium, sodium, potassium, magnesium, triethanolamine, diethanolamine and monoethanolamine. The alkyl sulfates are typically made by the sulfation of monohydric alcohols (having from about 8 to about 24 carbon atoms) using sulfur trioxide or other known sulfation technique. The alkyl ether sulfates are typically made as condensation products of ethylene oxide and monohydric alcohols (having from about 8 to about 24 carbon atoms) and then sulfated. These alcohols can be derived from fats, e.g., coconut oil or tallow, or can be synthetic. Specific examples of alkyl sulfates which may be used in the cleanser compositions are sodium, ammonium, potassium, magnesium, or TEA salts of lauryl or myristyl sulfate. Examples of alkyl ether sulfates which may be used include ammonium, sodium, magnesium, or TEA laureth-3 sulfate.

Another suitable class of anionic surfactants are the sulfated monoglycerides of the form $R^1CO$—$O$—$CH_2$—$C(OH)H$—$CH_2$—$O$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are typically made by the reaction of glycerin with fatty acids (having from about 8 to about 24 carbon atoms) to form a monoglyceride and the subsequent sulfation of this monoglyceride with sulfur trioxide. An example of a sulfated monoglyceride is sodium cocomonoglyceride sulfate.

Other suitable anionic surfactants include olefin sulfonates of the form $R^1$ $SO_3M$, wherein $R^1$ is a mono-olefin having from about 12 to about 24 carbon atoms, and M is a water-soluble cation such as ammonium, sodium, potassium, magnesium, triethanolamine, diethanolamine and monoethanolamine. These compounds can be produced by the sulfonation of alpha olefins by means of uncomplexed sulfur trioxide, followed by neutralization of the acid reaction mixture in conditions such that any sultones which have been formed in the reaction are hydrolyzed to give the corresponding hydroxyalkanesulfonate. An example of a sulfonated olefin is sodium $C_{14}$–$C_{16}$ alpha olefin sulfonate.

Other suitable anionic surfactants are the linear alkylbenzene sulfonates of the form $R^1$—$C_6H_4$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These are formed by the sulfonation of linear alkyl benzene with sulfur trioxide. An example of this anionic surfactant is sodium dodecylbenzene sulfonate.

Still other anionic surfactants suitable for this cleansing composition include the primary or secondary alkane sulfonates of the form $R^1SO_3M$, wherein $R^1$ is a saturated or unsaturated, branched or unbranched alkyl chain from about 8 to about 24 carbon atoms, and M is a water-soluble cation such as ammonium, sodium, potassium, magnesium, triethanolamine, diethanolamine and monoethanolamine. These are commonly formed by the sulfonation of paraffins using sulfur dioxide in the presence of chlorine and ultraviolet light or another known sulfonation method The sulfonation can occur in either the secondary or primary positions of the alkyl chain. An example of an alkane sulfonate useful herein is alkali metal or ammonium $C_{13}$–$C_{17}$ paraffin sulfonates.

Still other suitable anionic surfactants are the alkyl sulfosuccinates, which include disodium N-octadecylsulfosuccinamate; diammonium lauryl sulfosuccinate; tetrasodium N-(1,2-dicarboxyethyl)-N-octadecylsulfosuccinate; diamyl ester of sodium sulfosuccinic acid, dihexyl ester of sodium sulfosuccinic acid; and dioctyl esters of sodium sulfosuccinic acid.

Also useful are taurates which are based on taurine, which is also known as 2-aminoethanesulfonic acid. Examples of taurates include N-alkyltaurines such as the one prepared by reacting dodecylamine with sodium isethionate according to the teaching of U.S. Pat. No. 2,658,072 which is incorporated herein by reference in its entirety. Other examples based on taurine include the acyl taurines formed by the reaction of n-methyl taurine with fatty acids (having from about 8 to about 24 carbon atoms).

Another class of anionic surfactants suitable for use in the cleansing composition are the acyl isethionates The acyl isethionates typically have the formula $R^1CO$—$O$—$CH_2CH_2SO_3M$ wherein $R^1$ is a saturated or unsaturated, branched or unbranchad alkyl group having from about 10 to about 30 carbon atoms, and M is a cation. These are typically formed by the reaction of fatty acids (having from about 8 to about 30 carbon atoms) with an alkali metal isethionate. Nonlimiting examples of these acyl isethionates include ammonium cocoyl isethionate, sodium cocoyl isethionate, sodium lauroyl isethionate, and mixtures thereof.

Still other suitable anionic surfactants are the alkylglyceryl ether sulfonates of the form $R^1$—$OCH_2$—$C(OH)H$—$CH_2$—$SO_3M$, wherein $R^1$ is a saturated or unsaturated, branched or unbranched alkyl group from about 8 to about 24 carbon atoms, and M is a water-soluble cation such as ammonium, sodium, potassium, magnesium, triethanolamine, diethanolamine and monoethanolamine. These can be formed by the reaction of epichlorohydrin and sodium bisulfite with fatty alcohols (having from about 8 to about 24 carbon atoms) or other known methods. One example is sodium cocoglyceryl ether sulfonate.

Other suitable anionic surfactants include the sulfonated fatty acids of the form $R^1$—$CH(SO_4)$—$COOH$ and sulfonated methyl esters of the form $R^1$—CH(SO$_4$)—CO—O—CH$_3$, where $R^1$ is a saturated or unsaturated, branched or unbranched alkyl group from about 8 to about 24 carbon atoms. These can be formed by the sulfonation of fatty acids or alkyl methyl esters (having from about 8 to about 24 carbon atoms) with sulfur trioxide or by another known sulfonation technique. Examples include alpha sulphonated coconut fatty acid and lauryl methyl ester.

Other anionic materials include phosphates such as monoalkyl, dialkyl, and trialkylphosphate salts formed by the reaction of phosphorous pentoxide with monohydric branched or unbranched alcohols having from about 8 to about 24 carbon atoms. These could also be formed by other known phosphation methods. An example from this class of surfactants is sodium mono or dilaurylphosphate.

Other anionic materials include acyl glutamates corresponding to the formula $R^1$CO—N(COOH)—CH$_2$CH$_2$—CO$_2$M wherein $R^1$ is a saturated or unsaturated, branched or unbranched alkyl or alkenyl group of about 8 to about 24 carbon atoms, and M is a water-soluble cation. Nonlimiting examples of which include sodium lauroyl glutamate and sodium cocoyl glutamate.

Other anionic materials include alkanoyl sarcosinates corresponding to the formula $R^1$CON(CH$_3$)—CH$_2$CH$_2$—CO$_2$M wherein $R^1$ is a saturated or unsaturated, branched or unbranched alkyl or alkenyl group of about 10 to about 20 carbon atoms, and M is a water-soluble cation. Nonlimiting examples of which include sodium lauroyl sarcosinate, sodium cocoyl sarcosinate, and ammonium lauroyl sarcosinate.

Other anionic materials include alkyl ether carboxylates corresponding to the formula $R^1$—(OCH$_2$CH$_2$)$_x$—OCH$_2$—CO$_2$M wherein $R^1$ is a saturated or unsaturated, branched Or unbranched alkyl or alkenyl group of about 8 to about 24 carbon atoms, x is 1 to 10, and M is a water-soluble cation. Nonlimiting examples of which include sodium laureth carboxylate.

Other anionic materials include acyl lactylates corresponding to the formula $R^1$CO[O—CH(CH$_3$)—CO]$_x$—CO$_2$M wherein $R^1$ is a saturated or unsaturated, branched or unbranched alkyl or alkenyl group of about 8 to about 24 carbon atoms, x is 3, and M is a water-soluble cation. Nonlimiting examples of which include sodium cocoyl lactylate.

Other anionic materials include the carboxylates, nonlimiting examples of which include sodium lauroyl carboxylate, sodium cocoyl carboxylate, and ammonium lauroyl carboxylate. Anionic flourosurfactants can also be used.

Any counter cation, M, can be used on the anionic surfactant. Preferably the counter cation is selected from the group consisting of sodium, potassium, ammonium, monoethanolamine, diethanolamine, and triethanolamine. Ammonium has been found to provide higher levels of antimicrobial efficacy. However, it has been found to be less mild than other cations. Therefore, in some embodiments, levels of surfactant and proton donating agent must be adjusted accordingly. This is outlined in Table 1.

The anionic surfactants primarily employed in the compositions of the present invention can be grouped into four classes based on their mildness and antimicrobial efficacy. The four classes of anionic surfactants are defined below.

Class A—The first class of anionic surfactants are those which are considered to be mild, but minimally enhance antimicrobial efficacy. These includes the group consisting of alkyl ether sulfates; acyl monoglyceryl sulfates; alkyl glycerylether sulfonates; acyl isethionates; acyl taurates; alkyl sulfosuccinates; alkyl sulfoacetates; sulfonated olefins; alkyl sulfates which have a predominant chain length of C8, C10, C16 or C18; and mixtures thereof.

Class B—The second class of surfactants are those which are considered to be mild, but enhance antimicrobial efficacy. These include the group consisting of primary or secondary alkane sulfonates, alkyl sulfates which have a predominant chain length of C14, and mixtures thereof.

Class C—The third class of anionic surfactants are those which are considered to be harsh, but which greatly enhance antimicrobial efficacy. These include the group consisting of alkyl aryl sulfonates, alkyl sulfocarboxylates, sulfonated fatty acids, alkyl phosphates, alkyl sulfates which have a predominant chain length of C12, and mixtures thereof. Specific examples of harsh surfactants are lauryl sulfate, lauryl benzene sulfonate, monolauryl phosphate, and lauryl sulfocarboxylate.

It is beneficial to formulate compositions based on predominant mixtures of two of these classes at a time which comprise at least about 67%, preferably at least about 80%, more preferably about 90% of the anionic surfactant present in the liquid antimicrobial compositions herein Different ratios of surfactants in the different classes, result in required formulary adjustments. These are all summarized in Tables 1 and 2.

Nonlimiting examples of preferred anionic surfactants useful herein include those selected from the group consisting of sodium and ammonium alkyl sulfates and ether sulfates having chain lengths of predominantly 12 and 14 carbon atoms, olefin sulfates having chain lengths of predominantly 14 and 16 carbon atoms, and paraffin sulfonates having chain lengths of from 13 to 17 carbon atoms, and mixtures thereof. Especially preferred for use herein is ammonium and sodium lauryl sulfate; ammonium and sodium myristyl sulfate; ammonium and sodium laureth-1, laureth-2, laureth-3, and laureth-4 sulfate; ammonium and sodium, C14–C16 olefin sulfonates; C13–C17 paraffin sulfonates, and mixtures thereof.

Non-anionic surfactants of the group consisting of nonionic surfactants, cationic surfactants, amphoteric surfactants and mixtures thereof, have been found to actually reduce residual effectiveness benefits when used with anionic surfactants at high levels. This is most evident in the case of cationic and amphoteric surfactants where it is believed that these surfactants interfere (charge-charge interaction) with the anionic surfactant's ability to disrupt the lipid in the cell membrane. The ratio of the amount of these other surfactants to the amount of anionic surfactant should be less than 1:1, preferably less than 1:2, and more preferably less than about 1:4.

The rinse-off antimicrobial cleansing compositions of the present invention preferably do not comprise hydrotropic sulfonates, particularly salts of terpenoids, or mono- or binuclear aromatic compounds such as sulfonates of camphor, toluene, xylene, cumene and naphthene.

C. Proton Donating Agent

The rinse-off antimicrobial cleansing compositions of the present invention comprise from about 2% to about 10% based on the weight of the personal cleansing composition, of a proton donating agent. Preferable levels of proton donating agent are detailed in Tables 1 and 2. By "proton donating agent" it is meant any acid compound or mixture thereof, which results in the presence of undissociated acid on the skin after use. Proton donating agents can be organic acids, including polymeric acids, mineral acids or mixtures thereof. Straight chain $C_4$–$C_{20}$ fatty acids do not deliver the antimicrobial efficacy of the present invention. Therefore, rinse-off, antimicrobial composition, and thus the proton donating agent, must be essentially free of straight chain alkyl $C_4$–$C_{20}$ fatty acids.

Organic Acids

Proton donating agents which are organic acids, but not $C_4$–$C_{20}$ fatty acids, remain at least partially undissociated in the neat composition and remain so when the compositions are diluted during washing and rinsing. The organic acid proton donating agent must have at least one pKa value below 5.5. These organic proton donating agents can be added directly to the composition in the acid form or can be formed by adding the conjugate base of the desired acid and a sufficient amount of a separate acid strong enough to form the undissociated acid from the base.

Biological Activity Index of Organic Acids

Preferred organic proton donating agents are selected based on their biological activity. This activity is represented by a Biological Activity Index, Z, which is defined as:

$$Z = +0.25 pKa_1 + 0.42 \log P.$$

The biological activity index combines the dissociation characteristics and the hydrophobicity of the acid. It is critical that the undissociated proton donating agent of the composition be deposited on the skin to reduce the negative charge on the cell wall. The acid's dissociation constant $pKa_1$, is indicative of the chemical's proton donating capacity relative to the pH of the medium in which it is incorporated. Since more undissociated acid is preferable in the composition, acids with higher pKa's are generally more preferred for a given product pH. The octanol-water partition coefficient, P, represents the tendency of materials in solution to prefer either oils or water. It essentially is a measure of hydrophobic nature of a material in solution: the higher the partition coefficient, the more oil soluble, and less water soluble, the material. Since it is desired that the dissolved acids in the compositions come out of the aqueous cleanser upon application, deposit on the oil-based skin and remain during rinsing, organic acids with higher octanol-water partition coefficients are more preferred.

It has been found that $C_4$–$C_{20}$ alkyl fatty acids do not provide the antimicrobial effectiveness required of the present invention. Without being limited by theory, it is believed that surfactant nature of these fatty acids result in the formation of micels in presence of water. This micellular structure inhibits the antibacterial effects of the fatty acid.

Preferred organic proton donating agents of the rinse-off antimicrobial cleansing compositions of the present invention must be such that the antimicrobial composition is essentially free of $C_4$–$C_{20}$ alkyl fatty acids. By essentially free it is meant that the rinse-off antimicrobial compositions comprise less than about 0.5%, preferably less than 0.2%, more preferably less than 0.1%, and most preferably less than 0.05%. Further, these preferred organic proton donating agents have a biological activity index greater than about 0.75, preferably greater than about 1.0, more preferably greater than about 1.5 and most preferably greater than 2.0.

Mineral Acids

Proton donating agents which are mineral acids will not remain undissociated in the neat composition or when the compositions are diluted during washing and rinsing. Despite this, it has been found that mineral acids can be effective proton donating agents for use herein. Without being limited by theory, it is believed that the strong mineral acids, protonate the carboxylic and phosphatidyl groups in proteins of the skin cells, thereby providing in-situ undissociated acid. These proton donating agents can only be added directly to the composition in the acid form.

pH

It is critical to achieving the benefits of the invention that the undissociated acid from the proton donating agent (deposited or formed in-situ) remain on the skin in the protonated form. Therefore, the pH of the rinse-off antimicrobial cleansing compositions of the present invention must be adjusted to a sufficiently low level in order to either form or deposit substantial undissociated acid on the skin. The pH of the compositions should be adjusted and preferably buffered to have a range of from about 3.0 to about 5.5, preferred pH ranges are set forth in Tables 1 and 2.

A non-exclusive list of examples of organic acids which can be used as the proton donating agent are adipic acid, tartaric acid, citric acid, maleic acid, malic acid, succinic acid, glycolic acid, glutaric acid, benzoic acid, malonic acid, salicylic acid, gluconic acid, polyacrylic acid, their salts, and mixtures thereof. A non-exclusive list of examples of mineral acid for use herein are hydrochloric, phosphoric, sulfuric and mixtures thereof

D. Water

Liquid rinse-off antimicrobial cleansing compositions of the present invention comprise from about 35% to about 98.899%, preferably from about 45% to about 98%, more preferably from about 55% to about 97.5%, and most preferably from about 65% to about 93.9% water. Solid bar embodiments of the present invention preferably comprise from about 2% to about 25%, more preferably from about 3% to about 20% and most preferably from about 5% to about 15% water.

Liquid rinse-off antimicrobial cleansing compositions of the present invention, preferably have an apparent or neat viscosity of from about 500 cps to about 60,000 cps at 26.7° C., preferably 5,000 to 30,000 cps. The term "viscosity" as used herein means the viscosity as measured by a Brookfield RVTDCP with a spindle CP-41 at 1 RPM for 3 minutes, unless otherwise specified. The "neat" viscosity is the viscosity of the undiluted liquid cleanser.

E. Preferred Optional Ingredients

Mildness Enhancing Agents

In order to achieve the mildness required of the present invention, optional ingredients to enhance the mildness to the skin can be added. These ingredients include cationic and nonionic polymers, cosurfactants, moisturizers and mixtures thereof. Polymers useful herein include polyethylene glycols, polypropylene glycols, hydrolyzed silk proteins, hydrolyzed milk proteins, hydrolyzed keratin proteins, guar hydroxypropyltrimonium chloride, polyquats, silicone polymers and mixtures thereof. When used, the mildness enhancing polymers comprise from about 0.1% to about 1%, preferably from about 0.2% to about 1%, and more preferably from about 0.2% to about 0.6%, by weight of the rinse-off antimicrobial cleansing composition, of the composition. Cosurfactants useful herein include nonionic surfactants such as the Genapol® 24 series of ethoxylated alcohols, POE(20) sorbitan monooleate (Tween® 80), polyethylene glycol cocoate and Pluronic® propylene oxide/ethylene oxide block polymers, and amphoteric surfactants such as alkyl betaines, alkyl sultaines, alkyl amphoacetates, alkyl amphodiacetates, alkyl amphopropionates, and alkyl amphodipropionates. When used, the mildness enhancing cosurfactants comprise from about 20% to about 70%, preferably from about 20% to about 50%, by weight of the anionic surfactant, of the cleansing composition Preferred mildness enhancing agents are selected from the group of from about 20% to about 70%, by weight of the anionic surfactant, of the mildness enhancing cosurfactant, from about 0.1% to about 1.0%, by weight of the antimicrobial cleansing composition, of the mildness enhancing polymer, and mixtures thereof.

F. Other Optional Ingredients

The compositions of the present invention can comprise a wide range of optional ingredients The CTFA International Cosmetic Ingredient Dictionary, Sixth Edition, 1995, which is incorporated by reference herein in its entirety, describes a wide variety of nonlimiting cosmetic and pharmaceutical ingredients commonly used in the skin care industry, which are suitable for use in the compositions of the present invention. Nonlimiting examples of functional classes of ingredients are described at page 537 of this reference Examples of these functional classes include: abrasives, anti-acne agents, anticaking agents, antioxidants, binders, biological additives, bulking agents, chelating agents, chemical additives, colorants, cosmetic astringents, cosmetic biocides, denaturants, drug astringents, emulsifiers, external analgesics, film formers, fragrance components, humectants, opacifying agents, plasticizers, preservatives, propellants, reducing agents, skin bleaching agents, skin-conditioning agents (emollient, humectants, miscellaneous, and occlusive), skin protectants, solvents, foam boosters, hydrotropes, solubilizing agents, suspending agents (nonsurfactant), sunscreen agents, ultraviolet light absorbers, and viscosity increasing agents (aqueous and nonaqueous). Examples of other functional classes of materials useful herein that are well known to one of ordinary skill in the art include solubilizing agents, sequestrants, and keratolytics, and the like.

TABLE 1

Levels and Preferred Ranges for Antimicrobial Cleansing Compositions

| Primary Surfacants | Class A and Class C | Class A and Class C | Class A and Class C |
|---|---|---|---|
| NH$_4$ Counter Cation Content | | | |
| Preferred | Less than 50% | Greater than 50% | No limit |
| More Preferred | Less than 25% | Greater than 75% | |
| Surfactant Ratio | | | |
| Preferred | A:C from 4:1 to 1.5:1 | A:C from 5:1 to 2:1 | A:C from 1.5:1 to 1:1.5 |
| More Preferred | A:C from 3:1 to 1.5:1 | A:C from 4:1 to 2:1 | |
| Total Anionic Surfactant | | | |
| Preferred | 9% to 14% | 8% to 12% | 6% to 10% |
| % primary surfactant | | | |
| (by wt. of anionic surfactant) | greater than 67% | greater than 67% | greater than 67% |
| Preferred | greater than 80% | greater than 80% | greater than 80% |
| More Preferred | greater than 90% | greater than 90% | greater than 90% |
| Active Level | 0.1% to 5.0% | 0.1% to 5.0% | 0.1% to 5.0% |
| Preferred | 0.1% to 1.0% | 0.1% to 1.0% | 0.1% to 1.0% |
| Proton Donating Agent Level | 2% to 10% | 2% to 10% | 2% to 10% |
| Preferred | 4% to 8% | 4% to 10% | 4% to 10% |
| More Preferred | 4% to 6% | 4% to 8% | 4% to 8% |
| Composition pH | 3.0 to 5.5 | 3.0 to 5.5 | 3.0 to 5.5 |
| Preferred | 3.5 to 5.0 | 3.5 to 5.0 | 3.5 to 5.0 |
| More preferred | 3.5 to 4.5 | 3.5 to 4.5 | 3.5 to 4.5 |
| Cosurfactant Level - when used | | | |
| (by wt. of anionic surfactant) | | | |
| Preferred | 20% to 70% | 20% to 70% | 20% to 70% |
| More Preferred | 20% to 50% | 20% to 50% | 20% to 50% |
| Polymer Level - when used | | | |
| Preferred | 0.1% to 1.0% | 0.1% to 1.0% | 0.1% to 1.0% |
| More Preferred | 0.2% to 1.0% | 0.2% to 1.0% | 0.2% to 1.0% |
| Most Preferred | 0.2% to 0.6% | 0.2% to 0.6% | 0.2% to 0.6% |

TABLE 2

Levels and Preferred Ranges for Antimicrobial Cleansing Compositions

| Primary Surfactants | Class A and Class B | Class B and Class C |
|---|---|---|
| NH₄ Counter Cation Content | | |
| Preferred | No limit | No limit |
| More Preferred Surfactant Ratio | | |
| Preferred Total Anionic Surfactant | A:B from 100:0 to 1:2 | B:C from 100:0 to 1.2 |
| Preferred | 4% to 18% | 4% to 15% |
| More Preferred | 4% to 12% | 4% to 12% |
| % primary surfactant (by wt. of anionic surfactant) | greater than 67% | greater than 67% |
| Preferred | greater than 80% | greater than 80% |
| More Preferred | greater than 90% | greater than 90% |
| Active Level | 0.1% to 5.0% | 0.1% to 5.0% |
| Preferred | 0.1% to 1.0% | 0.1% to 1.0% |
| Proton Donating Agent Level | 2% to 10% | 2% to 10% |
| Preferred | 2% to 8% | 2% to 8% |
| Composition pH | 3.0 to 5.5 | 3.0 to 5.5 |
| Preferred | 3.5 to 5.0 | 3.5 to 5.0 |
| More Preferred | 3.5 to 4.5 | 3.5 to 4.5 |
| Cosurfactant Level - when used (by wt. of anionic surfactant) | | |
| Preferred | 20% to 70% | 20% to 70% |
| More Preferred | 20% to 50% | 20% to 50% |
| Polymer Level - when used | | |
| Preferred | 0.1% to 1.0% | 0.1% to 1.0% |
| More Preferred | 0.2% to 1.0% | 0.2% to 1.0% |
| Most Preferred | 0.2% to 0.6% | 0.2% to 0.6% |

II. METHODS OF MANUFACTURE OF RINSE-OFF ANTIMICROBIAL CLEANSING COMPOSITION

The rinse-off antimicrobial personal cleansing compositions of the present invention are made via art recognized techniques for the various forms of personal cleansing products.

III. METHODS OF USING THE RINSE-OFF ANTIMICROBIAL CLEANSING COMPOSITION

The rinse-off antimicrobial personal cleansing compositions of the present invention are useful for personal cleansing, especially for cleansing of the hands. Typically, a suitable or effective amount of the cleansing composition is applied to the area to be cleansed. Alternatively, a suitable amount of the cleansing composition can be applied via intermediate application to a washcloth, sponge, pat, cotton ball, puff or other application device. If desired, the area to be cleansed can be premoistened with water. The compositions of the present invention are combined with water during the cleansing process and rinsed-off from the skin. Generally, an effective amount of product to be used will depend upon the needs and usage habits of the individual. Typical amounts of the present compositions useful for cleansing range from about 0.1 mg/cm² to about 10 mg/cm², preferably from about 0.3 mg/cm² to about 3 mg/cm² skin area to be cleansed.

EXAMPLES

The following examples further describe and demonstrate embodiments within the scope of the present invention. In the following examples, all ingredients are listed at an active level. The examples are given solely for the purpose of illustration and are not to be construed as limitations of the present invention, as many variations thereof are possible without departing from the spirit and scope of the invention.

Ingredients are identified by chemical or CTFA name.

| Liquid Handsoap Component | Weight % | | | | |
|---|---|---|---|---|---|
| | 1 | 2 | 3 | 4 | 5 |
| Ammonium Lauryl Sulfate | 0.00 | 2.60 | 5.00 | 0.00 | 6.60 |
| Sodium Lauryl Sulfate | 3.50 | 0.00 | 0.00 | 0.00 | 0.00 |
| Ammonium Laureth-3 Sulfate | 0.00 | 7.90 | 0.00 | 5.20 | 5.20 |
| Sodium Laureth-3 Sulfate | 7.00 | 0.00 | 0.00 | 0.00 | 0.00 |
| $C_{14}$—$C_{16}$ Sodium Alpha Olefin Sulfonate | 0.00 | 0.00 | 0.00 | 7.40 | 0.00 |
| Sodium Myristyl Sulfate | 0.00 | 0.00 | 5.00 | 0.00 | 0.00 |
| Cocamidopropyl Betaine | 0.00 | 0.00 | 0.00 | 1.30 | 0.00 |
| Sodium Lauroamphoacetate | 5.25 | 5.25 | 3.00 | 0.00 | 0.00 |
| Citric Acid | 0.00 | 6.00 | 0.00 | 0.00 | 0,00 |
| Lactic Acid | 0.00 | 0.00 | 0.00 | 5.00 | 0.00 |
| Succinic Acid | 8.00 | 0.00 | 4.70 | 0.00 | 0.00 |
| Salicylic Acid | 0.00 | 0.00 | 0.00 | 0.00 | 2.00 |
| Sodium Citrate | 0.00 | to pH 3.7 | 0.00 | 0.00 | 0.00 |
| Polyquaternium 10 | 0.40 | 0.40 | 0.15 | 0.30 | 0.20 |
| Sodium Hydroxide | to pH 4.0 | 0.00 | to pH 4.0 | to pH 3.5 | to pH 4.5 |
| Para-chloro-meta-xylenol | 1.50 | 0.00 | 0.00 | 0.00 | 0.00 |
| Triclosan ® | 0.00 | 0.50 | 1.00 | 0.50 | 0.20 |
| Perfume | 1.0 | 1.0 | 0.00 | 1.0 | 1.0 |
| Water | Q.S. | Q.S. | Q.S. | Q.S. | Q.S. |

Procedure for Making Liquid Handsoap Examples

Add all but 5 weight percent water to mix tank. Add surfactants to mix tank. Heat materials to 155° F.±10° F. and mix until dissolved. Cool to less than 100° F., add acid and antibacterial active and perfumes. Mix until materials are dissolved. Adjust pH to target with required buffer (NaOH or sodium salt of acid). Add remaining water to complete product.

| Shower Gel Component | Weight % | | | | |
|---|---|---|---|---|---|
| | 1 | 2 | 3 | 4 | 5 |
| Sodium or Ammonium Lauryl Sulfate | 6.30 | 5.00 | 0.00 | 3.50 | 3.15 |
| Sodium or Ammonium Laureth-3 Sulfate | 4.20 | 15.00 | 5.80 | 7.00 | 9.45 |
| Sodium or Ammonium Lauroamphoacetate | 5.25 | 0.00 | 0.00 | 5.25 | 5.40 |
| Cocamide MEA | 2.80 | 0.00 | 0.00 | 2.80 | 0.00 |
| Cocamidopropyl Betaine | 0.00 | 0.00 | 5.20 | 0.00 | 0.00 |
| Citric Acid | 6.00 | 0.00 | 0.00 | 8.00 | 8.00 |
| Succinic Acid | 0.00 | 0.00 | 2.00 | 0.00 | 0.00 |
| Salicylic Acid | 0.00 | 2.00 | 2.00 | 0.00 | 0.00 |
| Triclorcarban ® | 0.00 | 0.15 | 0.00 | 0.00 | 0.00 |
| Triclosan ® | 1.00 | 0.25 | 0.00 | 0.60 | 0.60 |
| Thymol Oil | 0.00 | 0.00 | 2.00 | 0.00 | 0.00 |
| Sodium Hydroxide | 0.00 | to pH 4.5 | to pH 4.5 | to pH 3.7 | to pH 3.5 |
| Sodium Citrate | to pH 4 | 0.00 | 0.00 | 0.00 | 0.00 |
| Soybean Oil | 8.00 | 0.00 | 0.00 | 0.00 | 0.00 |
| Petrolatum | 0.00 | 0.00 | 0.00 | 0.00 | 16.50 |
| Polyquaternium 10 | 0.30 | 0.30 | 0.00 | 0.30 | 0.30 |
| Glycerine | 3.40 | 0.00 | 0.00 | 0.00 | 0.00 |
| Palmitic Acid | 2.20 | 0.00 | 0.00 | 0.00 | 0.00 |
| DMDM Hydantoin | 0.14 | 0.00 | 0.14 | 0.14 | 0.00 |
| Tetrasodium EDTA | 0.13 | 0.10 | 0.13 | 0.11 | 0.10 |
| Magnesium Sulfate | 1.10 | 0.00 | 0.00 | 0.00 | 0.00 |
| Sodium Chloride | 0.00 | 1.00 | 1.00 | 1.00 | 1.00 |
| Perfume | 1.3 | 1.3 | 0.4 | 0.5 | 0.50 |
| Dye | 0.01 | 0.01 | 0.01 | 0.00 | 0.01 |
| Water | Q.S. | Q.S. | Q.S. | Q.S. | Q.S. |

Procedure for Making Shower Gel Examples 1–4

Add moisturizing oils and cosurfactants together and heat ingredients to 130–140° F. until dissolved (step can be skipped for products not containing oils). In another container add primary surfactants, acid, buffer salt, preservatives, viscosity builder (salt), and polymer. Heat to 130–140° F. until dissolved. Combine two mixtures (or use single mixture if no oils are present) when both are 130–140° F., then begin cooling. When mixture is below 115° F., add, antibacterial active and perfume. Adjust final pH using NaOH or remaining buffer salt. Add remaining water to complete product.

Procedure for Making Shower Gel Examples 5

In a container add surfactants acid, buffer salt, preservatives, viscosity builder (salt), and polymer. Heat to 130–1404° F. until dissolved. Cool mixture to below 115° F., add antibacterial active, perfume, dye, and petrolatum. Adjust pH using NaOH or remaining buffer salt. Add remaining water to complete product.

| Bar Component | Wt % |
|---|---|
| Dextrin | 58.5 |
| Ammonium Laureth-3 Sulfate | 9.00 |
| Ammonium Lauryl Sulfate | 7.00 |

-continued

| Bar Component | Wt % |
|---|---|
| Lactic acid | 6.50 |
| Sodium Hydroxide | to pH 3.7 |
| Triclosan ® | 1.00 |
| Titanium Dioxide | 0.30 |
| Urea | 6.00 |
| Sorbitol | 0.30 |
| Sodium Chloride | 3.20 |
| Perfume | 1.00 |
| Water | Q.S. |

Procedure for Making Bar Example

The ingredients can be processed to form bars using conventional soap line equipment. For example, processing can be carried out as follows: First add the anionic surfactants to the crutcher. Next add the acid, and incorporate enough water such that the crutcher mixture is smooth fluid and has a manageable viscosity under agitation. Adjust the pH to target with required base (NaOH). Adjust the temperature of the mixture to 160–200° F. range. Next, introduce the dextrin into the mixture. Apply crutcher agitation and heat to again achieve a uniform composition at the above stated temperature range.

Pump the resulting mixture and spread it onto a conventional chill roll where the composition solidifies. Chip it off into a flake form. Convey the chips to an amalgamator where perfume and heat sensitive actives or components may be incorporated. Process the amalgamated flakes through a mill and plodder where they are extruded. Stamp into the desired bar shape.

| Hair Shampoo Component | Wt % |
| --- | --- |
| Ammonium Lauryl Sulfate | 7.00 |
| Ammonium Laureth-3 Sulfate | 9.00 |
| Sodium Lauroamphoacetate | 5.00 |
| Malic Acid | 2.00 |
| Salicylic Acid | 2.00 |
| Sodium Malate | to pH 4.5 |
| Pyrithione Zinc | 1.00 |
| Polyquaternium 10 | 0.50 |
| Perfume | 1.00 |
| Dye | 0.01 |
| Water | Q.S |

Procedure for Making Shampoo Examples

Add all but 5 weight percent water to mix tank. Add surfactants to mix tank. Heat materials to 155° F.±10° F. and mix until dissolved. Cool to less than 100° F., add acid, antibacterial active, perfumes and dyes. Mix until materials are dissolved. Adjust pH to target with required buffer (sodium salt of acid). Add remaining water to complete product.

| Liquid Laundry Detergent Component | Wt. % |
| --- | --- |
| $C_{13}$-$C_{17}$ Sodium Paraffin Sulfonate | 10.00 |
| Laureth-8 | 5.00 |
| Sodium Lauroamphodipropionate | 5.00 |
| Enzyme | 1.00 |
| Ethanol | 4.00 |
| Propylene Glycol | 6.00 |
| Polyquaternium-10 | 0.50 |
| Citric Acid | 6.00 |
| Triethanolamine | to pH 4.0 |
| Triclosan ® | 1.00 |
| Perfume | 1.00 |
| Water | Q.S. |

| Liquid Dish Detergent Component | Wt. % |
| --- | --- |
| $C_{13}$-$C_{17}$ Sodium Paraffin Sulfonate | 10.00 |
| Sodium Laureth-3 Sulfate | 5.00 |
| Cocoamidopropylhydroxysultaine | 5.00 |
| Polyquarternium-10 | 0.30 |
| Malic Acid | 6.00 |
| Sodium Hydroxide | to pH 4.5 |
| Para-chloro-meta-xylenol | 1.50 |
| Perfume | 1.00 |
| Water | Q.S. |

| Hard Surface Cleaner Component | Wt. % |
| --- | --- |
| $C_{14}$/$C_{16}$ Sodium Alpha Olefin Sulfonate | 4.00 |
| Acetic Acid | 4.00 |
| Ammonium Hydroxide | to pH 3.5 |
| o-phenylphenol | 0.25 |
| Perfume | 1.00 |
| Water | Q.S. |

Procedure for Making Above Examples

Add all but 5 weight percent water to mix tank. Add surfactants to mix tank. Heat materials to 155° F.±10° F. and mix until dissolved. Cool to less than 100° F., add acid, active and perfume. Mix until materials are dissolved. Measure and adjust pH to target with required buffer (NaOH or sodium salt of acid). Add remaining water to complete product.

What is claimed is:

1. A rinse-off antimicrobial cleansing composition comprising:
    a. from about 0.1% to about 5.0%, by weight of the cleansing composition, of an antimicrobial active;
    b. from about 9% to about 14%, by weight of the cleansing composition, of an anionic surfactant, wherein at least about 67% of the anionic surfactant is selected from the group consisting of Class A surfactants, Class C surfactants, and mixtures thereof, wherein the ratio of Class A surfactant to Class C is from about 4:1 to about 1.5:1, and wherein the total anionic surfactant comprises less than about 50% of the ammonium counter cation salt;
    c. from about 4% to about 8%, by weight of the cleansing composition, of a proton donating agent having a Biological Activity Index, Z, of greater than about 0.75, wherein the proton donating agent is such that the composition is essentially free of $C_4$–$C_{20}$ alkyl fatty acid;
    d. a mildness enhancing agent selected from the group consisting of from about 20% to about 70%, by weight of the anionic surfactant, of a mildness enhancing cosurfactant; from about 0.1% to about 1.0%, by weight of the cleansing composition, of a mildness enhancing polymer; and mixtures thereof; and
    e. from about 35% to about 93.9%, by weight of the cleansing composition, of water; wherein the composition is adjusted to a pH of greater than about 3.5 and less than about 4.5.

2. A rinse-off antimicrobial cleansing composition according to claim 1 wherein the mildness enhancing agent comprises from about 0.2% to about 0.6%, by weight of the cleansing composition, of a mildness enhancing polymer and from about 20% to about 50%, by weight of the anionic surfactant, of a mildness enhancing cosurfactant.

3. A rinse-off antimicrobial cleansing composition according to claim 2 wherein the antimicrobial active is selected from the group consisting of triclosan, triclocarban, piroctone olamine, PCMX, ZPT, natural essential oils and their key chemical components, and mixtures thereof.

4. A rinse-off antimicrobial cleansing composition according to claim 3 wherein the antimicrobial active triclosan.

5. A rinse-off antimicrobial cleansing composition according to claim 3 wherein the proton donating agent is an organic acid having a Biological Activity Index, Z, of greater than about 1.5.

6. A rinse-off antimicrobial cleansing composition according to claim 5 wherein the proton donating agent is selected from the group consisting of adipic acid, tartaric acid, citric acid, maleic acid, malic acid, succinic acid, glycolic acid, glutaric acid, benzoic acid, malonic acid, salicylic acid, gluconic acid, polyacrylic acid, hydrochloric acid, phosphoric acid, sulfuric acid, their salts, and mixtures thereof.

7. A rinse-off antimicrobial cleansing composition according to claim 6 wherein the ratio of the amount of non-anionic surfactants to the amount of anionic surfactant is less than 1:1.

8. A rinse-off antimicrobial cleansing composition according to claim 7 wherein the ratio of Class A surfactant to Class C surfactant is from about 3:1 to about 1.5:1.

9. A rinse-off antimicrobial cleansing composition comprising:
   a. from about 0.1% to about 5.0%, by weight of the cleansing composition, of an antimicrobial active;
   b. from about 8% to about 12%, by weight of the cleansing composition, of an anionic surfactant, wherein at least about 67% of the anionic surfactant is selected from the group consisting of Class A surfactants, Class C surfactants, and mixtures thereof, wherein the ratio of Class A surfactants to Class C surfactants is from about 5:1 to about 2:1, and wherein the anionic surfactant comprises greater than about 50% of the ammonium counter cation salt;
   c. from about 4% to about 10%, by weight of the cleansing composition, of a proton donating agent having a Biological Activity Index, Z, of greater than about 0.75, wherein the proton donating agent is such that the composition is essentially free of $C_4$–$C_{20}$ alkyl fatty acid;
   d. a mildness enhancing agent selected from the group consisting of from about 20% to about 70%, by weight of the anionic surfactant, of a mildness enhancing cosurfactant; from about 0.1% to about 1.0%, by weight of the cleansing composition, of a mildness enhancing polymer; and mixtures thereof; and
   e. from about 35% to about 93.9%, by weight of the cleansing composition, of water; wherein the composition is adjusted to a pH of greater than about 3.5 and less than about 5.0.

10. A rinse-off antimicrobial cleansing composition according to claim 9 wherein the mildness enhancing agent comprises from about 0.2% to about 0.6%, by weight of the cleansing composition, of a mildness enhancing polymer and from about 20% to about 50%, by weight of the anionic surfactant, of a mildness enhancing cosurfactant.

11. A rinse-off antimicrobial cleansing composition according to claim 10 wherein the antimicrobial active is selected from the group consisting of triclosan, triclocarban, piroctone olamine, PCMX, ZPT, natural essential oils and their key chemical components, and mixtures thereof.

12. A rinse-off antimicrobial cleansing composition according to claim 11 wherein the antimicrobial active is triclosan.

13. A rinse-off antimicrobial cleansing composition according to claim 12 wherein the proton donating agent is an organic acid having a Biological Activity Index, Z, of greater than about 1.5.

14. A rinse-off antimicrobial cleansing composition according to claim 13, wherein the proton donating agent is selected from the group consisting of adipic acid, tartaric acid, citric acid, maleic acid, malic acid, succinic acid, glycolic acid, glutaric acid, benzoic acid, malonic acid, salicylic acid, gluconic acid, polyacrylic acid, hydrochloric acid, phosphoric acid, sulfuric acid, their salts, and mixtures thereof.

15. A rinse-off antimicrobial cleansing composition according to claim 14 wherein the ratio of the amount of non-anionic surfactants to the amount of anionic surfactant is less than 1:1.

16. A rinse-off antimicrobial cleansing composition according to claim 15 wherein the ratio of Class A surfactant to Class C surfactant is from about 4:1 to about 2:1.

17. A rinse-off antimicrobial cleansing composition comprising:
   a. from about 0.1% to about 5.0%, by weight of the cleansing composition, of an antimicrobial active;
   b. from about 6% to about 10%, by weight of the cleansing composition, of an anionic surfactant, wherein at least about 67% of the anionic surfactant is selected from the group consisting of Class A surfactants, Class C surfactants, and mixtures thereof, wherein the ratio of Class A surfactants to Class C surfactants is from about 1.5:1 to about 1:1.5;
   c. from about 4% to about 10%, by weight of the cleansing composition, of a proton donating agent having a Biological Activity Index, Z, of greater than about 0.75 wherein less than about 50% of the proton donating agent is succinic acid, and wherein the proton donating agent is such that the composition is essentially free of $C_4$–$C_{20}$ alkyl fatty acid;
   d. a mildness enhancing agent selected from the group consisting of from about 20% to about 70%, by weight of the anionic surfactant, of a mildness enhancing cosurfactant; from about 0.1% to about 1.0%, by weight of the cleansing composition, of a mildness enhancing polymer; and mixtures thereof; and
   e. from about 35% to about 93.9%, by weight of the cleansing composition, of water;
   wherein the composition is adjusted to a pH of greater than about 3.5 and less than about 4.5.

18. A rinse-off antimicrobial cleansing composition according to claim 17 wherein the mildness enhancing agent comprises from about 0.2% to about 0.6%, by weight of the cleansing composition, of a mildness enhancing polymer and from about 20% to about 50%, by weight of the anionic surfactant, of a mildness enhancing cosurfactant.

19. A rinse-off antimicrobial cleansing composition according to claim 18 wherein the antimicrobial active is selected from the group consisting of triclosan, triclocarban, piroctone olamine, PCMX, ZPT, natural essential oils and their key chemical components, and mixtures thereof.

20. A rinse-off antimicrobial cleansing composition according to claim 19 wherein the antimicrobial active is triclosan.

21. A rinse-off antimicrobial cleansing composition according to claim 20 wherein the proton donating agent is an organic acid having a Biological Activity Index, Z, of greater than about 1.5.

22. A rinse-off antimicrobial cleansing composition according to claim 21 wherein the proton donating agent is selected from the group consisting of adipic acid, tartaric acid, citric acid, maleic acid, malic acid, succinic acid, glycolic acid, glutaric acid, benzoic acid, malonic acid, salicylic acid, gluconic acid, polyacrylic acid, hydrochloric acid, phosphoric acid, sulfuric acid, their salts, and mixtures thereof.

23. A rinse-off antimicrobial cleansing composition according to claim 22 wherein the ratio of the amount of non-anionic surfactants to the amount of anionic surfactant is less than 1:1.

24. A rinse-off antimicrobial cleansing composition comprising:
   a. from about 0.1% to about 5.0%, by weight of the cleansing composition, of an antimicrobial active;
   b. from about 4% to about 18%, by weight of the cleansing composition, of an anionic surfactant, wherein at least about 67% of the anionic surfactant is selected from the group consisting of Class B surfactants, Class C surfactants, and mixtures thereof, wherein the ratio of Class B surfactant to Class C is from about 100:0 to about 1:2;
   c. from about 2% to about 9%, by weight of the cleansing composition, of a proton donating agent having a Biological Activity Index, Z, of greater than about 0.75 wherein the proton donating agent is such that the composition is essentially free of $C_4$–$C_{20}$ alkyl fatty acid;
   d. from about 35% to about 93.9%, by weight of the cleansing composition, of water;
   wherein the composition is adjusted to a pH of greater than about 3.5 and less than about 4.5.

25. A rinse-off antimicrobial cleansing composition according to claim 24 further comprising a mildness enhancing agent selected from the group consisting of from about 20% to about 70%, by weight of the anionic surfactant, of a mildness enhancing cosurfactant; from about 0.1% to about 1.0%, by weight of the cleansing composition, of a mildness enhancing polymer, and mixtures thereof.

26. A rinse-off antimicrobial cleansing composition according to claim 25 wherein the antimicrobial active is selected from the group consisting of triclosan, triclocarban, piroctone olamine, PCMX, ZPT, natural essential oils and their key chemical components, and mixtures thereof.

27. A rinse-off antimicrobial cleansing composition according to claim 26 wherein the antimicrobial active is triclosan.

28. A rinse-off antimicrobial cleansing composition according to claim 27 wherein the proton donating agent is an organic acid having a Biological Activity Index, Z, of greater than about 1.5.

29. A rinse-off antimicrobial cleansing composition according to claim 28 wherein the proton donating agent is selected from the group consisting of adipic acid, tartaric acid, citric acid, maleic acid, malic acid, succinic acid, glycolic acid, glutaric acid, benzoic acid, malonic acid, salicylic acid, gluconic acid, polyacrylic acid, hydrochloric acid, phosphoric acid, sulfuric acid, their salts, and mixtures thereof.

30. A rinse-off antimicrobial cleansing composition according to claim 29 wherein the ratio of the amount of non-anionic surfactants to the amount of anionic surfactant is less than 1:1.

31. A rinse-off antimicrobial cleansing composition comprising:
   a. from about 0.1% to about 5.0%, by weight of the cleansing composition, of an antimicrobial active;
   b. from about 4% to about 18%, by weight of the cleansing composition, of an anionic surfactant, wherein at least about 67% of the anionic surfactant is selected from the group consisting of Class A surfactants, Class B surfactants, and mixtures thereof, wherein the ratio of Class A surfactant to Class B is from about 100:0 to about 1:2;
   c. from about 2% to about 8%, by weight of the cleansing composition, of a proton donating agent having a Biological Activity Index, Z, of greater than about 075 wherein the proton donating agent is such that the composition is essentially free of $C_4$–$C_{20}$ alkyl fatty acid;
   d. from about 35% to about 93.9%, by weight of the cleansing composition, of water;
   wherein the composition is adjusted to a pH of greater than about 3.5 and less than about 4.5.

32. A rinse-off antimicrobial cleansing composition according to claim 31 further comprising a mildness enhancing agent selected from the group consisting of from about 20% to about 70%, by weight of the anionic surfactant, of a mildness enhancing cosurfactant; from about 0.1% to about 1.0%, by weight of the cleansing composition, of a mildness enhancing polymer; and mixtures thereof.

33. A rinse-off antimicrobial cleansing composition according to claim 32 wherein the antimicrobial active is selected from the group consisting of triclosan, triclocarban, piroctone olamine, PCMX, ZPT, natural essential oils and their key chemical components, and mixtures thereof.

34. A rinse-off antimicrobial cleansing composition according to claim 33 wherein the antimicrobial active is triclosan.

35. A rinse-off antimicrobial cleansing composition according to claim 34 wherein the proton donating agent is an organic acid having a Biological Activity Index, Z, of greater than about 15.

36. A rinse-off antimicrobial cleansing composition according to claim 35 wherein the proton donating agent is selected from the group consisting of adipic acid, tartaric acid, citric acid, maleic acid, malic acid, succinic acid, glycolic acid, glutaric acid, benzoic acid, malonic acid, salicylic acid, gluconic acid, polyacrylic acid, hydrochloric acid, phosphoric acid, sulfuric acid, their salts, and mixtures thereof.

37. A rinse-off antimicrobial cleansing composition according to claim 36 wherein the ratio of the amount of non-anionic surfactants to the amount of anionic surfactant is less than 1:1.

38. A method for cleansing, reducing the number of germs on skin, and decreasing the spread of transient Gram negative and Gram positive bacteria comprising administering a safe and effective amount of the composition of claim 1 on human skin.

39. A method for cleansing, reducing the number of germs on skin, and decreasing the spread of transient Gram negative and Gram positive bacteria comprising administering a safe and effective amount of the composition of claim 9 on human skin.

40. A method for cleansing, reducing the number of germs on skin, and decreasing the spread of transient Gram negative and Gram positive bacteria comprising administering a safe and effective amount of the composition of claim 17 on human skin.

41. A method for cleansing, reducing the number of germs on skin, and decreasing the spread of transient Gram negative and Gram positive bacteria comprising administering a safe and effective amount of the composition of claim 24 on human skin.

42. A method for cleansing, reducing the number of germs on skin, and decreasing the spread of transient Gram negative and Gram positive bacteria comprising administering a safe and effective amount of the composition of claim 31 on human skin.

43. A method for treating acne comprising administering a safe and effective amount of the composition of claim 1 on human skin.

\* \* \* \* \*

UNITED STATES PATENT AND TRADEMARK OFFICE
CERTIFICATE OF CORRECTION

PATENT NO. : 6,451,333 B1
DATED : September 17, 2002
INVENTOR(S) : Peter William Beerse et al.

It is certified that error appears in the above-identified patent and that said Letters Patent is hereby corrected as shown below:

Column 22,
Line 67, "active" should read -- active is --.

Column 26,
Line 14, "075" should read -- 0.75 --.

Signed and Sealed this

Twenty-eighth Day of December, 2004

JON W. DUDAS
*Director of the United States Patent and Trademark Office*